United States Patent [19]

Lebo et al.

[11] Patent Number: 5,723,593
[45] Date of Patent: Mar. 3, 1998

[54] DIAGNOSTIC ASSAY FOR CHARCOT MARIE TOOTH DISEASE TYPE 1B

[75] Inventors: Roger V. Lebo, San Francisco, Calif.; Jeffrey V. Ravetch, New York, N.Y.

[73] Assignee: The Regents of the University of California, Oakland, Calif.

[21] Appl. No.: 485,479

[22] Filed: Jun. 7, 1995

Related U.S. Application Data

[63] Continuation-in-part of Ser. No. 91,336, Jul. 13, 1993.
[51] Int. Cl.[6] ............................ C07H 21/02; C12Q 1/68
[52] U.S. Cl. ............................................ 536/23.1; 435/6
[58] Field of Search ........................... 435/6; 935/77, 935/78; 536/23.1

[56] References Cited

U.S. PATENT DOCUMENTS 4,683,195  7/1987  Urden et al. ........................ 435/6

OTHER PUBLICATIONS

Hayasaka et al, Biochem. Biophy. Res. Comm 180: 515–518 (1991).

*Primary Examiner*—Eggerton A. Campbell
*Attorney, Agent, or Firm*—Townsend and Townsend and Crew LLP

[57] ABSTRACT

The present invention provides compositions, methods and kits for the detection of genetic polymorphisms or mutations related to Charcot-Marie-Tooth Disease Type 1B. The polymorphism or mutations generally occur in the protein P0 gene in chromosome 1. Also provided are mutant forms of protein P0 and methods for screening compounds to identify compounds that enhance binding between mutant P0 proteins.

24 Claims, 8 Drawing Sheets

Figure 4. AMINO ACID COMPARISON OF PO GENES

```
            50        60 61          75 76         90 91 K96X    105
HUMAN...CSFWSSEWVSD DISFTWRYQPEGGRD AISIFHYAKGQPYID EVGTFKERIQWVGDP...
RAT   ...CSVWSSEWVSD DISFTWRYQPEGGRD AISIFHYAKGQPYID EVGTFKERIQWVGDP...
COW   ...CSVWSSEWVSD DLSFTWRYQPEGGRD AISIFHYAKGQPYID EVGTFKERIQWVGDP...
CMT1B...                                        ...EVGTFKERIZWVGDP...
```

RAT: total of 94% identity to human in 240 aa overlap
COW: total of 93% identity to human in 219 aa overlap AA# 1-153      Extracellular domain in myelin intraperiod line
AA# 154-179    Transmembrane Domain
AA# 180-240    Cytoplasmic domain in major dense line UNDERLINED sequences are identical to human.

DIAGNOSTIC ASSAY FOR CHARCOT MARIE TOOTH DISEASE TYPE 1B

This is a continuation in part of U.S. Ser. No. 08/091,336, filed Jul. 13, 1993, which is incorporated herein by reference.

This invention was made with Government support under Grant No. 9-R01-AI34662-06, awarded by the National Institute of Health. The Government has certain rights in this invention.

BACKGROUND OF THE INVENTION

The present invention relates generally to detecting the presence of genetic polymorphisms or mutations associated with Charcot-Marie-Tooth Disease Type 1B (CMT1B). More particularly, the present invention provides compositions and methods for identifying CMT1B-associated polymorphisms or mutations in patient nucleic acid samples by amplification of patient nucleic acid and identifying CMT1B-associated point mutations in the amplification products.

Over 2000 human diseases are known to result from DNA alterations including deletions, multiplications and nucleotide substitutions. Finding genetic disease alterations in individuals and following these alterations in families provides a means to confirm clinical diagnoses and to diagnose disease in carriers, preclinical and subclinical affected individuals, affected unborn fetuses, fetal cells in maternal blood, and preimplantation embryos. Counselling based upon accurate diagnoses allows patients to make informed decisions about potential parenting, ongoing pregnancy, and early intervention in affected individuals.

Disease associated deletions, multiplications, and nucleotide substitutions may be large or small. Polymorphisisms at disease sites can be used to trace abnormal allelic segregation. However, normal polymorphic nucleotide changes can complicate detection of abnormal alleles with changes at different nucleotides. Because multiple alleles within genes are common, one must distinguish disease-related alleles from neutral (non-disease-related) mutations. Most alleles result from neutral mutations that produce indistinguishable, normally active gene products or express normally variable characteristics like eye color. In contrast, some alleles are associated with clinical disease like sickle cell anemia. Disease-related mutations may result from a single point mutation as occurs in sickle cell anemia.

Previously diagnosis and confirmation of genetic disease and carrier states often relied upon enzyme activity testing, statistical analysis, or invasive diagnostic procedures. For example, painful nerve conduction tests have been necessary to detect preclinical and subclinical cases of Type 1 Charcot-Marie-Tooth Disease. Such invasive physiological testing is not available for identifying disease in fetuses.

DNA polymorphisms or mutations (RFLPs; Restriction fragment length polymorphism or mutations) have been used to diagnose more than 20 genetic diseases (See Lebo et al, *Am. J. Hum. Genet.* 47:583–590, (1990)). The DNA Committee of the Pacific Southwest Regional Genetics Network proposed that a prenatal clinical test must be informative in at least 70% of fetuses and must be at least 95% reliable (Ibid.). The percent informative matings are calculated according to Chakravarti and Buetow, *Am. J. Hum. Genet.* 37:984–997 (1985), with different formulas for autosomal recessive, autosomal dominant, and X-linked genetic disease. Not all matings are informative because parents may be homozygous for neutral DNA polymorphisms or mutations. The proportion of informative matings depend upon 1) the number of different alleles at each gene locus, 2) the relative frequency of each allele in the population (the most informative have more than one common allele), and 3) whether alleles are distributed randomly throughout the population. Finding enough informative polymorphisms or mutations can be very laborious when few or uncommon polymorphisms or mutations are found at a disease locus (Lebo et al, *Am. J. Hum. Genet.* 47:583–590 (1990)). Using characterized polymorphisms or mutations may be laborious since several often need to be tested. See, e.g., Lebo et al, *Am. J. Med. Genet.* 37:187–190, (1990). Even then a proportion of uninformative results in some pedigrees are anticipated.

Charcot-Marie-Tooth disease (CMT, Hereditary Motor and Sensory Neuropathy, HMSN) is the most common generic neuropathy with an incidence of 1/2600 (Skre, *Clin. Genet.*, 6:98–118 (1974)). Genetically heterogeneous CMT subtypes are clinically similar with pes cavus, distal muscle weakness and atrophy, absent or diminished deep tendon reflexes, and mild sensory loss. CMT Type I (CMT1, HMSNI) is a demyelinating peripheral neuropathy with slower nerve conduction velocities while Type II (CMT2, PMSNII) is a non-demyelinating neuronal disorder with near normal nerve conduction velocities (Dyck and Lambert, *Arch. Neurol.* 18:603–618 (1968) and Dyck and Lambert, *Clin. Neurol.*, 18:619–625 (1968)). The more severe CMT1 tends to be manifested in late childhood or adolescence and progress slowly but inexorably (Bird and Kraft, *Clin. Genet.*, 14:43–49 (1978); Vanasse and Dubowitz, *Muscle and Nerve*, 4:26–30 (1981)). CMT has been mapped to chromosome 1 (Bird et al., *Am. J. Hum. Genet.*, 34:388–394 (1982); Guiloff et al., *Ann. Hum. Genet.*, 46:25–27 (1982); Stebbens & Cormsally, *Am. J. Hum. Genet.*, 34:195 (1982)), chromosome 17 (Vance et al., *Expt. Neurology*, 104:186–189 (1989); Lebo et al., *Am. J. Hum. Genet.*, 50:42–45 (1992)), chromosome X (Gal et al., *Hum. Genet.*, 70:38–42 (1985); Beckett et al., *J. Neurogenet.*, 3:225–231 (1986); Fischbeck et al., *An. Neuron.*, 20:527–532 (1986); Ionasescu et al., *Am. J. Hum. Genet.*, 48:1075–1083 (1991)), and another autosomal locus (Chance et al., *J. Hum. Genet.*, 47:915–925 (1990)). Chromosome 17 CMT1A is usually associated with a 1.5 Mb duplication (Lupsky et al., Cell, 66:219–232 (1991); Raeymaekers et al., *Neuromuscular Disorders*, 1:93–97 (1991); Hoogendijk et al., *Human Genet.*, 88:215–218 (1991)) spanning the peripheral myelin protein gene (PMP22; Patel et al., *Nature Genetics*, 1:159–165 (1992); Timmerman et al., *Nature Genetics*, 1:166–170 (1992); Othman et al., *Nature Genetica*, 1:171–175 (1992); Matsunami et al., *Nature Genetics*, 1:176–179 (1992)). Mutant PMP22 without duplication also results in clinical CMT1A (Valentija et al., *Nature Genetics*, 2:288–291 (1992)). Genetic mutations associated with CMT1B have not been published. Therefore, methods of genetic screening and diagnosis have not become available to clinicians and patients suspected of having CMT1B. Because genetic testing has not been available, painful nerve conduction studies have been required to make or confirm the diagnosis of CMT1B. Further, no methods of pre-natal testing have been available.

What is needed in the art is a rapid and reliable method to detect genetic abnormalities associated with CMT1B. The method should be applicable to pre- and post-natal patient samples. Use of such a test could provide a means for prenatal diagnosis of affected fetuses and provide more accurate and less painful diagnosis of living patients. Quite surprisingly the present invention fulfills these and other related needs.

SUMMARY OF THE INVENTION

The present invention provides methods, compositions and kits for the detection of genetic polymorphisms or mutations associated with Charcot-Marie-Tooth Disease Type 1B. The compositions generally comprise amplification primers that span a polymorphic exon of the gene encoding protein P0 on chromosome 1. Typically, the primers will be homologous to genomic P0 gene sequences.

The present invention also provides methods for the presence of a genetic polymorphism or mutation and allele specific mutations associated with Charcot-Marie-Tooth Disease Type 1B in a sample of patient nucleic acid. The methods generally comprise amplifying a subsequence of the patient nucleic acid to produce an amplification product; and identifying the presence of a Charcot-Marie-Tooth Disease Type 1B associated polymorphism or mutation in the amplification product. Generally, the DNA of the CMT 1B gene region in the protein P0 gene will be amplified by polymerase chain reaction to produce amplification products that contain the polymorphic region. The polymorphisms and allele-specific mutations may be detected by a variety of methods including restriction enzyme analysis of the amplification product, sequencing the amplification product, separating the amplification product on a denaturing gel, and detecting different polymorphic regions with sequence specific oligonucleotide probes.

Kits are also provided for practicing the present invention. The kits comprise a vial containing amplification primers that span the target polymorphic region. The kits may also include a thermostable polymerase, other amplification reagents, and specific size markers for gel electrophoresis.

DEFINITIONS

To aid in understanding the invention, several terms are defined below.

"Amplification reaction mixture" refers to an aqueous solution comprising the various reagents used to amplify a target nucleic acid. These include: enzymes, aqueous buffers, salts, target nucleic acid, and deoxynucleoside triphosphates. Depending upon the context, the mixture can be either a complete or incomplete amplification reaction mixture and the primers may be a single pair or nested primer pairs.

"Amplification reagents" refer to the various buffers, enzymes, primers, deoxynucleoside triphosphates (both conventional and unconventional), and primers used to perform the selected amplification procedure.

"Amplifying" or "Amplification", which typically refers to an "exponential" increase in target nucleic acid, is being used herein to describe both linear and exponential increases in the numbers of a select target sequence of nucleic acid.

"Bind(s) substantially" refers to complementary hybridization between an oligonucleotide and a target sequence and embraces minor mismatches that can be accommodated by reducing the stringency of the hybridization media to achieve the desired priming for the PCR polymerases or detection of hybridization signal.

The phrase "biologically pure" refers to material that is substantially or essentially free from components which normally accompany it as found in its native state. For instance, affinity purified antibodies or monoclonal antibodies exist in a biologically purified state.

As used to refer to nucleic acid sequences, the term "homologous" indicates that two or more nucleotide sequences share a majority of their sequence. Generally, this will be at least about 70% of their sequence and preferably at least 95% of their sequence. Another indication that sequences are substantially identical is if they hybridize to the same nucleotide sequence under stringent conditions (see, e.g., Sambrook et al., *Molecular Cloning—A Laboratory Manual*, Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

As used to refer to proteins or polypeptides, the term "homologous" is meant to indicate two proteins or polypeptides share a majority of their amino acid sequences. Generally, this will be at least 90% and usually more than about 95%.

"Hybridizing" refers the binding of two single stranded nucleic acids via complementary base pairing.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Nucleotide polymerases" refers to enzymes able to catalyze the synthesis of DNA or RNA from a template strand using nucleoside triphosphate precursors. In the amplification reactions of this invention, the polymerases are template-dependent and typically add nucleotides to the 3'-end of the polymer being synthesized. It is most preferred that the polymerass is thermostable as described in U.S. Pat. No. 4,889,819, incorporated herein by reference.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors including the ultimate function or use of the oligonucleotide. Oligonucleotides can be prepared by any suitable method, including, cloning and restriction of appropriate sequences and direct chemical synthesis by a method such as the phosphotriester method of Narang et al., 1979, *Meth. Enzymol.* 69:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each of which is incorporated herein by reference.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template.

The term "primer" may refer to more than one primer, particularly in the case where there is some ambiguity in the information regarding one or both ends of the target region to be amplified. For instance, if a region shows significant levels of polymorphism or mutation in a population, mixtures of primers can be prepared that will amplify alternate sequences. A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

"Probe" refers to an oligonucleotide which binds through complementary base pairing to all or part of a target nucleic acid. It will be understood by one of skill in the art that probes will typically substantially bind target sequences lacking complete complementarity with the probe sequence depending upon the stringency of the hybridization conditions. The probes are preferably directly labelled as with isotopes or indirectly labelled such as with biotin to which an avidin or streptavidin complex may later bind. By assaying for the presence or absence of the probe, one can detect the presence or absence of the target.

"Recombinant" when referring to a nucleic acid probe refers to an oligonucleotide which is free of native proteins and nucleic acid typically associated with probes isolated from the cell, which naturally contains the probe sequence as a part of its native genome. Recombinant probes include those made by amplification means such as PCR and genetic cloning methods where bacteria are transformed or infected with the recombinant probe.

The term "reverse transcriptase" refers to an enzyme that catalyses the polymerization of deoxynucleoside triphosphates to form primer extension products that are complementary to a ribonucleic acid template. The enzyme initiates synthesis at the 3'-end of the primer and proceeds toward the 540 -end of the template until synthesis terminates. Examples of suitable polymerizing agents that convert the RNA target sequence into a complementary, DNA (cDNA) sequence are arian myeloblastosis virus reverse transcriptase and *Thermus thermophilus* DNA polymerase, a thermostable DNA polymerase with reverse transcriptase activity marketed by Perkin Elmer Cetus, Inc.

As used herein, the term "sample" refers to a collection of biological material from an organism containing nucleated cells. This biological material may be solid tissue as from a fresh or preserved organ or tissue sample or biopsy; blood or any blood constituents; bodily fluids such as amniotic fluid, peritoneal fluid, or interstitial fluid; cells from any time in gestation including an unfertilized ovum or fertilized embryo, preimplantation blastocysts, or any other sample with intact interphase nuclei or metaphase cells no matter what ploidy (how many chromosomes are present). The "sample" may contain compounds which are not naturally intermixed with the biological material such as preservatives anticoagulants, buffers, fixatives, nutrients, antibiotics, or the like.

The terms "sequence-specific oligonucleotide" and "SSO" refer to oligonucleotides that have a sequence, called a "hybridizing region," exactly complementary to the sequence to be detected, typically sequences characteristic of a particular allele or variant, which under "sequence-specific, stringent hybridization conditions" will hybridize only to that exact complementary target sequence. Relaxing the stringency of the hybridizing conditions will allow sequence mismatches to be tolerated; the degree of mismatch tolerated can be controlled by suitable adjustment of the hybridization conditions. Depending on the sequences being analyzed, one or more sequence-specific oligonucleotides may be employed. The terms "probe" and "SSO probe" are used interchangeably with SSO.

A "sequence specific to" a particular target nucleic acid sequence is a sequence unique to the isolate, that is, not shared by other previously characterized isolates. A probe containing a subsequence complementary to a sequence specific to a target nucleic acid sequence will typically not hybridize to the corresponding portion of the genome of other isolates under stringent conditions (e.g., washing the solid support in 2×SSC, 0.1% SDS at 70° C.).

"Subsequence" refers to a sequence of nucleic acids that comprise a part of a longer sequence of nucleic acids.

The term "target region" refers to a region of a nucleic acid to be analyzed and may include a polymorphic sites.

The term "thermostable polymerass enzyme" refers to an enzyme that is relatively stable when heated and catalyzes the polymerization of nucleoside triphosphates to form primer extension products that are complementary to one of the nucleic acid strands of the target sequence. The enzyme initiates synthesis at the 3'-end of the primer and proceeds toward the 5'-end of the template until synthesis terminates. A purified thermostable polymerass enzyme is described more fully in U.S. Pat. No. 4,889,818, incorporated herein by reference, and is commercially available from Perkin-Elmer Cetus Instruments (Norwalk, Conn.).

BRIEF DESCRIPTION OF THE FIGURES

FIG. 4 illustrates a comparison of encoded of amino acids in the CMT1B-associated polymorphic region of the protein P0 gene.

DETAILED DESCRIPTION OF SPECIFIC EMBODIMENTS

Figure 1A:
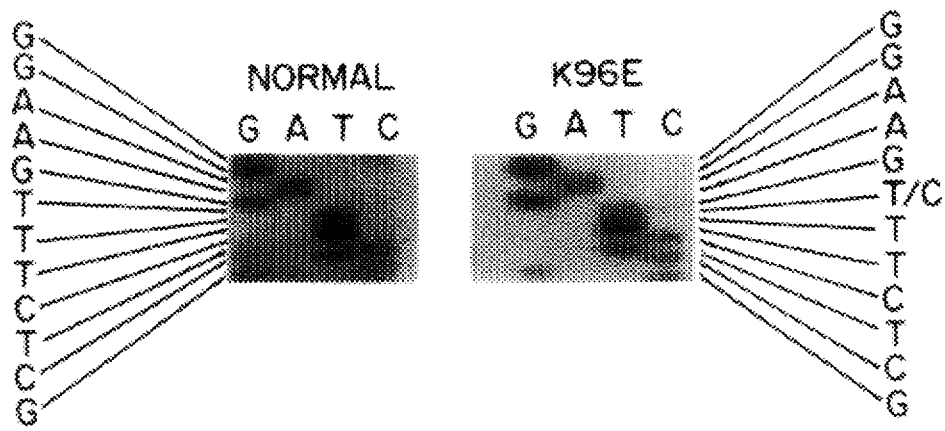
FIG. 1 illustrates normal and mutant protein P0 sequences.

The present invention provides compositions and methods for detecting genetic abnormalities associated with CMT1B. CMT1B-associated polymorphisms or mutations in patient nucleic acid samples are detected by amplification of patient nucleic acid and identifying CMT1B-associated point mutations within the amplified fragments. The mutations occur at the chromosome locus encoding protein P0 and its regulatory sequences. P0 is an adhesive myelin transmembrane protein that maintains myelin structure. Mutations of protein P0 may result in the clinical signs and symptoms of demyelinating CMT1B.

The devastating effects of myelin loss result in both peripheral and central neuropathies such as Guillain-Barre syndrome and multiple sclerosis, respectively (Ropper et al., *Guillain Barre Syndrome*, F. A. Davis Co., Philadelphia, (1991); McDonald et al., *Multiple Sclerosis*, Butterworth, London, (1986)). The P0 protein functions as a double adhesion molecule with extracellular and cytoplasmic interactions that hold together the myelin sheath (Filbin and Tennekoon, *BioEssays*, 14:541–547 (1992)). Since P0 is expressed exclusively in the peripheral nervous system in myelinating Schwann cells and composes >50% of the myelin protein, abnormal P0 protein may cause the peripheral demyelination seen in CMT1B.

Protein P0 is a homophilic double adhesion molecule that maintains myelin membrane. Peripheral myelin P0 structural protein is expressed exclusively in the peripheral nervous system in myelinating Schwann cells. The protein accounts for over 50% of the myelin protein (Eylar et al., *Neurochem. Res.*, 4:289–293 (1979)). The schwann cell lays down insulating cytoplasmic membrane sheets with each sheet including an intracellular major dense line between adjacent single membranes and an extracellular intraperiod line between pairs of cytoplasmic membranes. The mature P0 protein has a cytoplasmic domain in the major dense line (Uyemurs & Kitamura, *Comp. Biochem. Physiol.*, 98c:63–72 (1991)), a transmembrane domain, and an extracellular domain in the intraperiod line (Lemke et al., *Cell*, 40:501–508 (1985) and Uyemura & Kitamura, supra) that hold together the myelin membrane. Cultured HeLa cells transfected with the P0 gene express P0 on the cytoplasmic membrane that migrates to the point of membrane contact between touching cultured cells to act as an adhesive to maintain cell contact (Filbin & Tennekoon, *BioEssays*, 4:541–547 (1992)). Cultured Schwann cells infected with retrovirus carrying antisense P0 cDNA insheath exons but are unable to myelinate (Owens & Boyd, *Development*, 112:639–649 (1991)).

The human gene encoding protein P0 is located on the long arm of chromosome 1. The gene contains 6 exons. Exon 3 has been found to contain a highly conserved region that contains a point mutation in affected individuals in the largest known CMT1B pedigree. The region of this mutation is highly conserved in at least three mammalian orders. Other polymorphisms or mutations in intron, exon, or regulatory regions of the gene encoding protein P0 may also be associated with CMT1B.

Missense point mutations of the gene encoding protein P0 are present in the affected individuals of the CMT1B largest pedigree. The point mutations result in substitution of a negatively charged glutamic acid (E) for a positively charged lysine (K) in this highly conserved extracellular protein region. Substitution of a negatively charged amino acid for a positive one in this protein region required for adhesive binding to another P0 protein represents a major change most likely to disrupt P0 extracellular domain attachment.

The present invention provides compositions for detecting nucleic acid sequences containing polymorphisms or mutations in nucleic acid sequences encoding protein P0 that are associated with CMT1B. The compositions contain nucleic acid sequences useful as primers for polymerass chain reaction amplification of the polymorphic alleles. Sample oligonucleotide sequences of the hybridizing regions of the primers of the invention are presented below. Those skilled in the art will realize that an oligonucleotide sequence used as the hybridizing region of a primer can also be used as the hybridizing region of a probe. Suitability of a primer sequence for use as a probe depends on the hybridization characteristics of the primer. Similarly, an oligonucleotide used as a probe can be used as a primer. The compositions may comprise oligonucleotide primers substantially homologous to one of the following nucleic acid sequences:

TTC CAC TAT GCC AAG GGA CAA C; (SEQ ID NO:1)
CTG GTG GGT TTT TGA CAT CAC AT (SEQ ID NO:2).

or any other suitable sequences identical to the genomic human or mouse P0 nucleotide sequences. Generally, the compositions contain both SEQ ID NO:1 and SEQ ID NO:2. Other amplification primers may be employed to detect the same or other CMT1B-related polymorphisms or mutations in nucleic acid sequences encoding protein P0. Knowledge that P0 mutations may cause CMT1B provides a basis for persons of skill to identify other CMT1B-related polymorphisms or mutations in protein P0 encoding sequences by methods described below. Amplification primers may be identified by computer programs, such as Primer version 0.5 (Whitehead Institute of Biomedical Research, 1991).

The primers of the present invention may be employed in methods for detecting the presence of a genetic polymorphism or mutation associated with Charcot-Marie-Tooth Disease Type 1B in nucleic acid encoding protein P0 in a sample of patient nucleic acid. The methods generally comprise amplifying a P0-encoding subsequence of the patient nucleic acid to produce an amplification product; and identifying the presence of a Charcot-Marie-Tooth Disease Type 1B associated polymorphism or mutation in the amplification product. Generally, the patient nucleic acid will be chromosomal DNA of chromosome 1, but segments of cDNA or RNA may be amplified and analyzed by the methods of the present invention.

In a preferred embodiment, the primers of the invention are used in conjunction with a polymerass chain reaction (PCR) amplification of the target nucleic acid. Although the PCR process is well known in the art (see U.S. Pat. Nos. 4,683,195; 4,683,202; and 4,965,188, each of which is incorporated herein by reference) and although commercial vendors, such as Perkin Elmer Cetus, Inc., sell PCR reagents and publish PCR protocols, some general PCR information is provided below for purposes of clarity and full understanding of the invention for those unfamiliar with the PCR process.

The methods of the present invention may be employed for analyzing nucleic acid from a variety of different tissues. If PCR is used to amplify the target regions in blood cells, whole blood should be drawn with an anticoagulant in a sealed vacuum tube kept separated from other samples and handled with clean gloves. For best results, blood should be processed immediately after collections if this is impossible, it should be kept in a sealed container until use. Cells in other physiological fluids, such as amniotic fluid, may also be assayed. When using any of these fluids, the cells in the fluid should be separated from the fluid component by centrifugation.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples are known in the art. For example, see those described in Rotbart et al., 1989, in *PCR Technology* (Erlich ed., Stockton Press, New York) and Han et al., 1987, *Biochemistry* 26:1617–1625. The methods described by Fries et al., *Am. J. Med. Genet.*, 46:363–368 (1993), incorporated herein by reference, are also useful.

Several methods are particularly well suited for use in amplifying target regions of chromosome 1. The choice between these methods is typically governed by the size of the sample which is available for testing. One method is crude extraction which is useful for relatively large samples.

Briefly, mononuclear cells from samples of blood, buffy coat, amniocytes from amniotic fluid, cultured chorionic villus cells, or the like are isolated by standard procedures. If testing DNA from peripheral blood lymphocytes, an osmotic shock treatment or denaturing cellular protein (Fines et al., 1993). If PCR testing is not performed immediately after sample collection, aliquots of $10^6$ cells can be pelleted in sterile Eppendorf tubes and the dry pellet frozen at $-20°$ C. or colder until use.

The blood cells are resuspended ($10^6$ nucleated cells per 100 µl) in a buffer of 50 mM Tris-HCl (pH 8.3), 50 mM KCl 1.5 mM $MgCl_2$, 0.5% Tween 20, 0.5% NP40 supplemented with 100 µg/ml of proteinase K. After incubating at 56° C. for 2 hr, the cells are heated to 95° C. for 10 min to inactivate the proteinase K and immediately moved to wet ice (snap-cool). If gross aggregates are present, another cycle of digestion in the same buffer should be undertaken. Ten µl of this extract is generally used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60°C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR may be employed to amplify target regions of chromosome 1 in very small numbers of cells (1000–5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids. Res.*, 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2EDTA$, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and mixed gently. The DNA precipitate is removed from the ethanol and air dried. The precipitate is placed in distilled water and dissolved.

Kits are also commercially available for the extraction of high-molecular weight DNA for PCR. These kits include Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA may be determined by spectrophotometric analysis of the absorbance of a diluted aliquot at 260 nm and 280 nm. Either 10 µof crude extract, or 1 µg of purified DNA by the alternate methods are used for PCR amplification.

The first step of each cycle of the PCR involves the separation of the nucleic acid duplex formed by the primer extension. Of course, if the target nucleic acid is single-stranded, i.e., single-stranded RNA, no initial separation step is required. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for an sufficient time to cause the denaturation of the duplex but not to cause an irreversible denaturation of the polymerase (see U.S. Pat. No. 4,965, 188). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology* 43:63–67; and Radding, 1982, *Ann. Rev. Genetics* 16:405–436, both of which are incorporated herein by reference).

Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In some instances, protein P0-encoding RNA may be used as the initial template for primer extension is RNA. Polymerizing agents suitable for synthesizing a complementary, DNA (cDNA) sequence from the RNA template are reverse transcriptase (RT), such as avian myeloblastosis virus RT, Moloney murine leukemia virus RT, or

*Thermus thermophilus* (Tth) DNA polymerass, a thermostable DNA polymerass with reverse transcriptase activity marketed by Perkin Elmer Cetus, Inc. Typically, the RNA template is heat degraded during the first denaturation step after the initial reverse transcription step leaving only DNA template. Suitable polymerases for use with a DNA template include, for example, *E. coli* DNA polymerass I or its Klenow fragment, $T_4$ DNA polymerass, Tth polymerase, and Taq polymerass, a heat-stable DNA polymerass isolated from *Thermus aquaticus* and commercially available from Perkin Elmer Cetus, Inc. The latter enzyme is widely used in the amplification and sequencing of nucleic acids. The reaction conditions for using *Taq* polymerass are known in the art and are described in Gelfand, 1989, *PCR Technology, supra*.

When RNA is amplified, an initial reverse transcription (RT) step is carried out to create a DNA copy (cDNA) of the RNA. PCT patent publication No. WO 91/09944, published Jul. 11, 1991, incorporated herein by reference, describes high-temperature reverse transcription by a thermostable polymerass that also functions in PCR amplification. High-temperature RT provides greater primer specificity and improved efficiency. A "homogeneous RT-PCR" in which the same primers and polymerase suffice for both the reverse transcription and the PCR amplification steps, and the reaction conditions are optimized so that both reactions occur without a change of reagents is also available. *Thermus thermophilus* DNA polymerase, a thermostable DNA polymerase that can function as a reverse transcriptase, is used for all primer extension steps, regardless of template. Both processes can be done without having to open the tube to change or add reagents; only the temperature profile is adjusted between the first cycle (RNA template) and the rest of the amplification cycles (DNA template).

The PCR method can be performed in a step-wise fashion, where after each step new reagents are added, or in a fashion where all of the reagents are added simultaneously, or in a partial step-wise fashion, where fresh or different reagents are added after a given number of steps. For example, if strand separation is induced by heat, and the polymerass is heat-sensitive, then the polymerase has to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region, and an extension reaction region. Alternatively, the annealing and extension temperature can be the same. Reverse transcriptase-PCR uses such a two-step temperature cycling. A machine specifically adapted for use with a thermostable enzyme is commercially available from Perkin Elmer Cetus, Inc.

Those skilled in the art will also be aware of the problems of contamination of a PCR by the amplified nucleic acid from previous reactions and nonspecific amplification. Methods to reduce these problems are provided in PCT patent application Ser. No. 91/05210, filed Jul. 23, 1991, incorporated herein by reference. The method allows the enzymatic degradation of any amplified DNA from previous reactions and reduces nonspecific amplification. The PCR amplification is carried out in the presence of dUTP instead of dTTP. The resulting double-stranded, uracil-containing product is subject to degradation by uracil N-glycosylase (UNG), whereas normal thymine-containing DNA is not degraded by UNG. Adding UNG to the amplification reaction mixture before the amplification is started degrades all uracil-containing DNA that might serve as target. Because the only source of uracil-containing DNA is the amplified product of a previous reaction, this method effectively sterilizes the reaction mixture, eliminating the problem of contamination from previous reactions (carry-over). UNG itself is rendered temporarily inactive by heat, so the denaturation steps in the amplification procedure also serve to inactivate the UNG. New amplification products, therefore, though incorporating uracil, are formed in an effectively UNG-free environment and are not degraded.

Those practicing the present invention should note that, although the preferred embodiment incorporates PCR amplification, amplification of target sequences in a sample may be accomplished by any known method, such as ligase chain reaction (LCR), transcription amplification, and self-sustained sequence replication, each of which provides sufficient amplification so that the target sequence can be detected by nucleic acid hybridization to an SSO probe. Persons of skill will appreciate that in methods such as LCR, primers that are complementary to the specific polymorphism or mutation are required. In this instance amplification only occurs if the polymorphism or mutation is present in the nucleic acid sample.

Alternatively, methods that amplify the probe to detectable levels can be used, such as Qβ-replicase amplification. The term "probe" encompasses the sequence specific oligonucleotides used in the above procedures; for instance, the two or more oligonucleotides used in LCR are "probes" for purposes of the present invention, even though some embodiments of LCR only require ligation of the probes to indicate the presence of an allele.

A variety of methods may be employed to analyze the nucleotide sequence of the amplification products. Several techniques for detecting point mutations following amplification by PCR have been described in Chehab et al., *Methods in Enzymology*, 216:135–143 (1992); Maggio et al., *Blood*, 81(1):239–242 (1993); Cai and Kan, *Journal of Clinical Investigation*, 85(2):550–553 (1990) and Cai et al., *Blood*, 73:372–374 (1989), each of which is incorporated herein by reference.

One particularly useful technique is analysis of restriction enzyme sites following amplification. In this method, amplified nucleic acid segments are subjected to digestion by restriction enzymes. Identification of differences in restriction enzyme digestion between corresponding amplified segments in different individuals may identify a point mutation. Differences in the restriction enzyme digestion is commonly determined by sizes of the restriction fragments by electrophoresis and observing differences in the electrophoretic patterns. Generally, the sizes of the restriction fragments will be determined by standard gel electrophoresis techniques as described in Sambrook et al., *Molecular Cloning, A Laboratory Manual*, Cold Spring Harbor Press, 1989, and Polymeropoulos et al., *Genomics*, 12:492–496 (1992), both of which are incorporated herein by reference. Polyacrylamide gel electrophoresis is particularly preferred because of its capability of high discrimination.

Briefly, aliquots of the amplification reaction mixture are placed on a gel with sizing markers, such as sequencing ladders. Following electrophoresis, the amplified products are visualized and identified. Generally, the gels are stained with ethidium bromide and the size of the restriction fragments are compared with molecular markers. Alternatively, autoradiography may be employed to simultaneously visualize and identify the amplified products. Amplification may be run with labelled nucleotide bases that provide a means for identifying the amplified segments following the procedure. Alternatively, labelled nucleic acid primers may employed as labelling probes which can hybridize to the amplified segments following electrophoresis. Typical autoradiographic labels include $^{32}P$, $^{14}C$, $^{3}H$, $^{125}I$, $^{35}S$, or the like. Alternatively, probes may be labelled with visual labels such as photoluminescence, or fluorescent probes like Texas red, rhodamine and its derivatives, red leuco dye and 3,3',5,5'-tetramethylbenzidine (TMB), fluorescein and its derivatives, dansyl, umbelliferone and the like, or with enzymes like horseradish peroxidase, alkaline phosphatase, or the like.

The size of the amplified segments are compared to the size of the amplified regions of affected and normal individuals. One polymorphism related to CMT1B occurs in exon 3 of the gene encoding protein P0. A point mutation introduces a unique restriction site not present in nucleic acid encoding normal protein P0. The amplifed segments containing this polymorphism have a BstBI restriction site that is absent in normal persons. PAGE analysis demonstrates a 163 base pair amplified segment in normal individuals following BstBI digestion while affected individuals carrying this polymorphism exhibit 115 and 48 base pair segments following BstBI digestion. Because of the high discrimination of the polyacrylamide gel electrophoresis, differences of this magnitude are easily detected. Other mutations resulting in CMT1B-related polymorphisms of protein P0 encoding genes may also add unique restriction sites to the gene that can be determined by sequencing CMT1B-related nucleic acid sequences and comparing them to normal sequences.

Another useful method of detecting point mutations in PCR products employs denaturation and renaturation on denaturing gels. Use of denaturing gels is well known in the art as described in Sambrook et al, supra, previously incorporated herein by reference.

Another useful method of identifying point mutations in PCR amplification products employs oligonucleotide probes specific for different sequences. The oligonucleotide probes are mixed with amplification products under hybridization conditions. Probes may be either RNA or DNA oligonucleotides or polynucleotides and may contain not only naturally occurring nucleotides but their analogs like digoxygenin dCTP, biotin dCTP, 7-azaguanosine, azidothymidine, inosine, or uridine. The advantages of analogs include greater stability, resistance to nuclease activity, ease of signal attachment, increased protection from extraneous contamination and an increased number of probe-specific colored labels.

Probes may be generated and chosen by several means including mapping by in situ hybridization (Landegent et al, *Nature* 317:175–177, 1985), somatic cell hybrid panels (Ruddle & Creagan, *Ann. Rev. Genet.* 9:431, 1981), or spot blots of sorted chromosomes (Lebo et al, *Science* 225:57–59, 1984); chromosomal linkage analysis (Ott, *Analysis of Human Genetic Linkage*, Johns Hopkins Univ Press, pp. 1–197,1985); or cloned and isolated from sorted chromosome libraries from human cell lines or somatic cell hybrids with human chromosomes (Deaven et al, *Cold Spring Harpor Symp.* LI:159–168, 1986; Lebo et al. *Cold Spring Harbor Symp.* LI:169–176), radiation somatic cell hybrids (Cox et al, *Am. J. Hum. Genett* 43:A141, 1988), microdissection of a chromosome region (Claussen et al, *Cytometry* 11:suppl 4 p. 12, 1990), (all of which are incorporated by reference), or from yeast artificial chromosomes (YACs) identified by PCR primers specific for a unique chromosome locus (sequence tagged site or STS) or other suitable means like an adjacent YAC clone. Probes may be genomic DNA, cDNA, or viral DNA cloned in a plasmid, phage, cosmid, YAC, or any other suitable vector. Probes may be cloned or synthesized chemically. When cloned, the isolated probe nucleic acid fragments are typically inserted into a replication vector, such as lambda phage, pBR322, M13, pJB8, c2RB, pcos1EMBL, or vectors containing the SP6 or T7 promoter and cloned as a library in a bacterial host. General probe cloning procedures are described in Arrand J. E., *Nucleic Acid Hybridization A Practical Approach*, Hames B. D., Higgins, S. J., Eds., IRL Press 1985, pp. 17–45 and Sambrook, J., Fritsch, E. F., Maniatis, T., *Molecular Cloning A Laboratory Manual*, Cold Spring Harbor Press, 1989, pp. 2.1–3.58, both of which are incorporated herein by reference.

Briefly, the DNA sequences to be cloned are partially or completely digested by cloning-site specific restriction enzyme digestion of selected nucleic acids. The ends of the DNA sequences to be cloned may be modified to minimize ligation to other DNA fragments but still permit ligation to the vector. Other modifications may be made prior to ligation to the vector like blunt ending or addition of homopolymer tails or oligonucleotide linkers. Vector nucleic acids must be cleaved with appropriate restriction enzymes to specifically open the cloning site. The resulting DNA fragments are recovered and tested for ligating efficiency. Acceptable DNA fragments to be cloned are ligated to the acceptable vector. The resulting ligated DNA sequences may then be processed appropriately for the chosen vector. Generally, ligated plasmids are transformed into bacteria, or packaged into a bacteriophage and transfected into bacteria, or introduced into yeast. The bacteria are plated and screened for clones carrying the sequences of interest or pools of yeast clones are grown and the DNA extracted. Then clones are plated in an array, grown, and screened with sequence-specific probe. Selected clones are grown and probes extracted by cell lysis and nucleic acid extraction followed by gel electrophoresis, high pressure liquid chromatography, or low or high speed column or gradient centrifugation. Pulsed field gel electrophoresis may be preferred to isolate a pure YAC clone.

Alternatively, oligonucleotide probes may be synthesized chemically with or without fluorochromes, chemically active groups on nucleotides, or labeling enzymes using commercially available methods and devices like the Model 380B DNA synthesizer from Applied Biosystems, Foster City, Calif., using reagents supplied by the same company. Other methods may also be used to synthesize oligonucleotide probes, e.g., the solid phase phosphoramidite method that produces probes of about 15–250 bases. Methods are detailed in Caruthers et al., *Cold Spring Harbor Symp. Ouant. Biol.*, 47:411–418, 1982, and Adams, et al., *J. Am. Chem. Soc.*, 105:661, 1983, both of which are incorporated herein by reference.

Probes may be selected by using commercially available computer programs to compare known DNA sequences from genes sequences found in libraries like Genebank and EMBL. The programs identify unique nucleotide sequences within the gene of interest. One such program is Eugene. Oligonucleotide sequences for PCR of a unique chromosome region can be chosen optimally by choosing sequences according to previously established protocols or by computer programs that choose the degree of homology desired along with the length of the probe. Sequences are chosen to avoid technical problems like primer dimers resulting from amplification of hybridized primers.

Probes may be labeled with several fluorophors or enzymes that generate colored products. This allows simultaneous use of probes to different CMT1B-related polymorphisms or mutations. Identification of hybridization of a specifically labelled probe provides a means for determining which polymorphism or mutation is present in the nucleic acid of the sample. The probes used in the assay must be labeled with more than one distinquishable fluorescent or pigment color. Probes may be labeled with Texas red, rhodamine and its derivatives, fluorescein and its derivatives, dansyl, umbelliferone and the like or with horse radish peroxidase, alkaline phosphatase, biotin, avidin, or the like.

Probes can be labeled directly or indirectly. The common indirect labeling schemes covalently bind a ligand to the nucleotide and prepare labeled probe by incorporating this using random priming or nick translation. The ligand then binds an anti-ligand which is covalently bound to a label. Ligands and anti-ligands vary widely. When a ligand has an anti-ligand, e.g., biotin, thyroxine, or cortisol, the ligand may be used in conjunction with the labelled naturally-occurring anti-ligand. Alternatively, a hapten or antigen may be used in combination with an antibody.

Sequence specific oligonucleotide probes hybridize specifically with a particular segment of the target polymorphism or mutation amplification products and have destabilizing mismatches with the sequences from other polymorphisms or mutations. Under sufficiently stringent hybridization conditions, the probes hybridize specifically only to exactly complementary sequences. The stringency of the hybridization conditions can be relaxed to tolerate varying amounts of sequence mismatch. Detection of the amplified product utilizes this sequence-specific hybridization to insure detection of only the correct amplified target, thereby decreasing the chance of a false positive caused by the presence of homologous sequences from related polymorphisms or mutations.

The assay methods for detecting hybrids formed between SSO probes and nucleic acid sequences can require that the probes contain additional features in addition to the hybridizing region. For example, if the probe is first immobilized, as in the "reverse" dot blot format described below, the probe can also contain long stretches of poly-dT that can be fixed to a nylon support by irradiation, a technique described in more detail in PCT Patent Publication No. 89/11548, incorporated herein by reference. In the dot blot format, immobilized target is hybridized with probes containing a compound used in the detection process, as discussed below.

The probes of the invention can be synthesized and labeled using the techniques described above for synthesizing oligonucleotides. The probe can be labeled at the 5'-end with $^{32}P$ by incubating the probe with $^{32}P$-ATP and kinase. A suitable nonradioactive label for SSO probes is horseradish peroxidase (HRP). Methods for preparing and detecting probes containing this label are described in U.S. Pat. Nos. 4,914,210 and 4,962,029, both of which are incorporated herein by reference. For additional information on the use of such labeled probes, see U.S. Pat. No. 4,789,630; Saiki et al., 1988, *N. Eng. J. Med.* 319:537–541; and Bugawan et al., 1988, *Bio/Technology* 943–947, each of which is incorporated herein by reference. Useful chromogens include red leuco dye and 3,3',5,5'-tetramethylbenzidine (TMB).

The probes of the invention can be used to determine if specific polymorphisms or mutations are present in a sample by determining if the SSO probes bind to the nucleic acid sequences present in the sample. Suitable assay methods for purposes of the present invention to detect hybrids formed between SSO probes and nucleic acid sequences in a sample are known in the art. For example, the detection can be accomplished using a dot blot format as generally described in Sambrook et al., supra, previously incorporated herein by reference. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with a single probe, the dot blot format is quite useful. Many samples can be immobilized at discrete locations on a single membrane and hybridized simultaneously by immersing the membrane in a solution of probe.

An alternate method that is quite useful when large numbers of different probes are to be used is a "reverse" dot blot format, in which the amplified sequence contains a label, and the probe is bound to the solid support. This format would be useful if the test of the present invention were used as one of a battery of tests to be performed simultaneously. In this format, the unlabeled SSO probes are bound to the membrane and exposed to the labeled sample under appropriately stringent hybridization conditions. Unhybridized labeled sample is then removed by washing under suitably stringent conditions, and the filter is then monitored for the presence of bound sequences.

Both the forward and reverse dot blot assays can be carried out conveniently in a microtiter plate. The probes can be attached to bovine serum albumen (BSA), for example, which adheres to the microliter plate, thereby immobilizing the probe. Another suitable assay system entails adding a labeled probe to the amplification reaction mixture during the PCR amplification process. Any SSO probe that hybridizes to target DNA during each synthesis step is degraded by the 5' to 3' exonuclease activity of a polymerase, e.g., Taq polymerase. The degradation product from the probe is then detected. Thus, the presence of the breakdown product indicates that the hybridization between the SSO probe and the target DNA occurred.

Specific protein P0-encoding polymorphisms or mutations may also be identified by sequencing the amplification products or restriction fragments thereof. Sequencing may be performed by a variety of methods well known in the art. For example, the sequence of the amplified nucleic acid segments may be determined by the Maxam-Gilbert chemical degradation method as described in Sambrook et al., *Molecular Cloning, A Laboratory Manual*, supra, previously incorporated herein by reference. Generally, Sanger dideoxy-mediated sequencing will be employed as also described in Sambrook et al., supra.

Briefly, the amplified nucleic acid segments are used as templates for DNA synthesis. At least four separate synthesis reactions are employed. Each synthesis reaction mixture contains an excess of dNTPs. Chain-terminating dideoxynucleoside triphosphates (ddNTP) are included in the synthesis reaction mixture. Each reaction mixture contains a different ddNTP, i.e., ddTTP, ddCTP, ddGTP, and ddATP. The syntheses are performed allowing for random incorporation of the ddNTP. Synthesis terminates upon incorporation of ddNTP in the chain. Therefore, following a sufficient period of template replication, fragments of nucleic acid sequences which terminating at each nucleotide base will be present in the synthesis reaction mixtures. Fragments which terminate at ATP will be present in the reaction mixture containing ddATP, fragments terminating at GTP will be present in the reaction mixture containing ddGTP, etc. The fragments in the reaction mixtures separated by size on a gel and identified by labeled bases incorporated during synthesis. The pattern of the separated fragments on the gels provides a means to determine the nucleic acid sequence of the amplified segments. Sequencing may also be performed by automated sequencing devices or commercially available sequencing kits such as the ΔTag Cycle Sequencing Kit available from United States Biochemical.

The present invention provides mutated forms of protein P0. By "mutated forms of protein P0", it is meant proteins or polypeptides that share at least about 65% with protein P0 in persons not affected by CMT1B, yet differ by at least one amino acid. The difference between the mutated form of protein P0 and normal protein P0 may be a deletion, insertion, or substitution. One mutated form of protein P0 of the present invention is a point mutation at amino acid 96 of the P0 amino acid sequence reported in Hayasaka et al., *Biochem. Biophys. Res. Commun.*, 180:515–518 (1991), incorporated herein by reference. Hereinafter, this mutated protein is referred to as P0-mutl.

The present invention also provides methods for identifying compounds that enhance adhesion between mutated forms of protein P0. The methods generally comprise contacting the compound of interest with at least two molecules of a protein as described above; and determining the affinity of binding between the binding proteins. As mutations that affect the homophilic character of protein P0 are associated with CMT1B, developing compounds that enhance adhesion of mutated forms of protein P0 may provide therapeutic relief of demyelination associated with CMT1B. Compounds designed to bind complementary regions of mutated forms of protein P0 may developed by computer modelling of the structures of mutated protein P0 molecules and computer aided drug design.

The present invention also provides kits for the detection of genetic polymorphisms or mutations associated with Charcot-Marie-Tooth Disease Type 1B. The kits comprise a vial containing amplification primers that span a CMT1B-associated polymorphism or mutation in the gene encoding protein P0. For example, the vial may contain SEQ ID NO:1 and SEQ ID NO:2. The kits may also contain a vial containing a thermostable polymerase, genetic size markers for gels, and amplification reagents.

The following examples are offered by way of illustration and not limitation.

EXAMPLES

Example 1

This example demonstrates identification of a polymorphism or mutation of the gene encoding protein P0 that is associated with CMT1B. The mutation-containing polymorphism was found to be present in the largest known CMT1B pedigree.

Patient peripheral blood samples were obtained with informed consent from over 100 large and small CMT pedigrees as described in Lebo et al., *Human Genet.*, 88:1–12 (1991) and Lebo et al., *Human Genet.*, 88:13–20 (1991), both of which are incorporated herein by reference. Peripheral blood lymphocyte DNAs were extracted directly or from Epstein-Barr transformed peripheral blood lymphocyte cultures as described in Lebo et al., *Human Genet.*, 88:1–12 (1991).

Potential nucleic acid amplification primers were identified by analysis of six mouse protein P0 exons. The analysis was performed according to the computer program Primer version 0.5 (Whitehead Inst. Biomed. Res., (1991)). Amplification was performed by polymerase chain reaction. Seperate amplifications were performed employing each set of primers.

Two of fourteen primer sites identified by Primer detected human P0 sequence abnormality. To 25 picomoles each of Exon 3 primers P03F: TTC CAC TAT CCC AAG GGA CAA C and P03R: CTG GTG GGT TTT TGA CAT CAC AT were added 50–250 ng sample DNA in 16.6 mM $(NH_4)_2SO_4$, 67 mM tris-HCl (pH 8.8), 6.7 mM $MgCl_3$, 10 mM 2-mercaptoethanol, 170 mg/ml BSA, 6.8 mM EDTA buffer, 1.67 mM of each dNTP, and 2% DMSO and Taq polymerase. The DNA was denatured at 94° C. for 5 min and then amplified by denaturing 40 sec at 95° C., annealing 1 min at 60° C., elongating 1 min at 72° C. for each of 30 cycles.

Amplified nucleic acid segments were digested according to manufacturer's recommended conditions with 40 Units BstB1 at 65° C. for 4 hrs (New England Biolabs). The restriction fragments were resolved by 9% acrylamide gel electrophoresis, stained with ethidium bromide, and photographed.

Figure 1B:
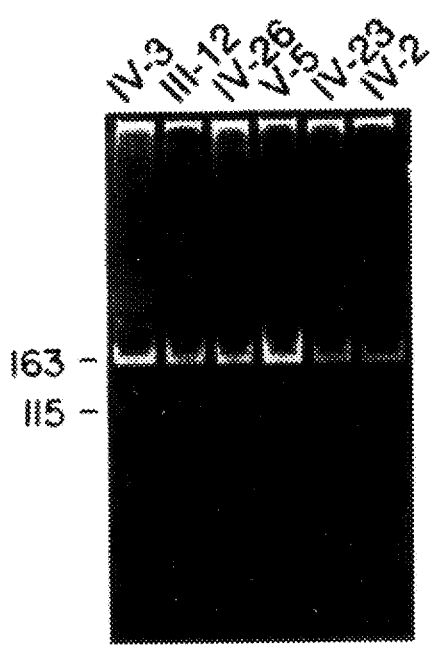
Figure 2A:
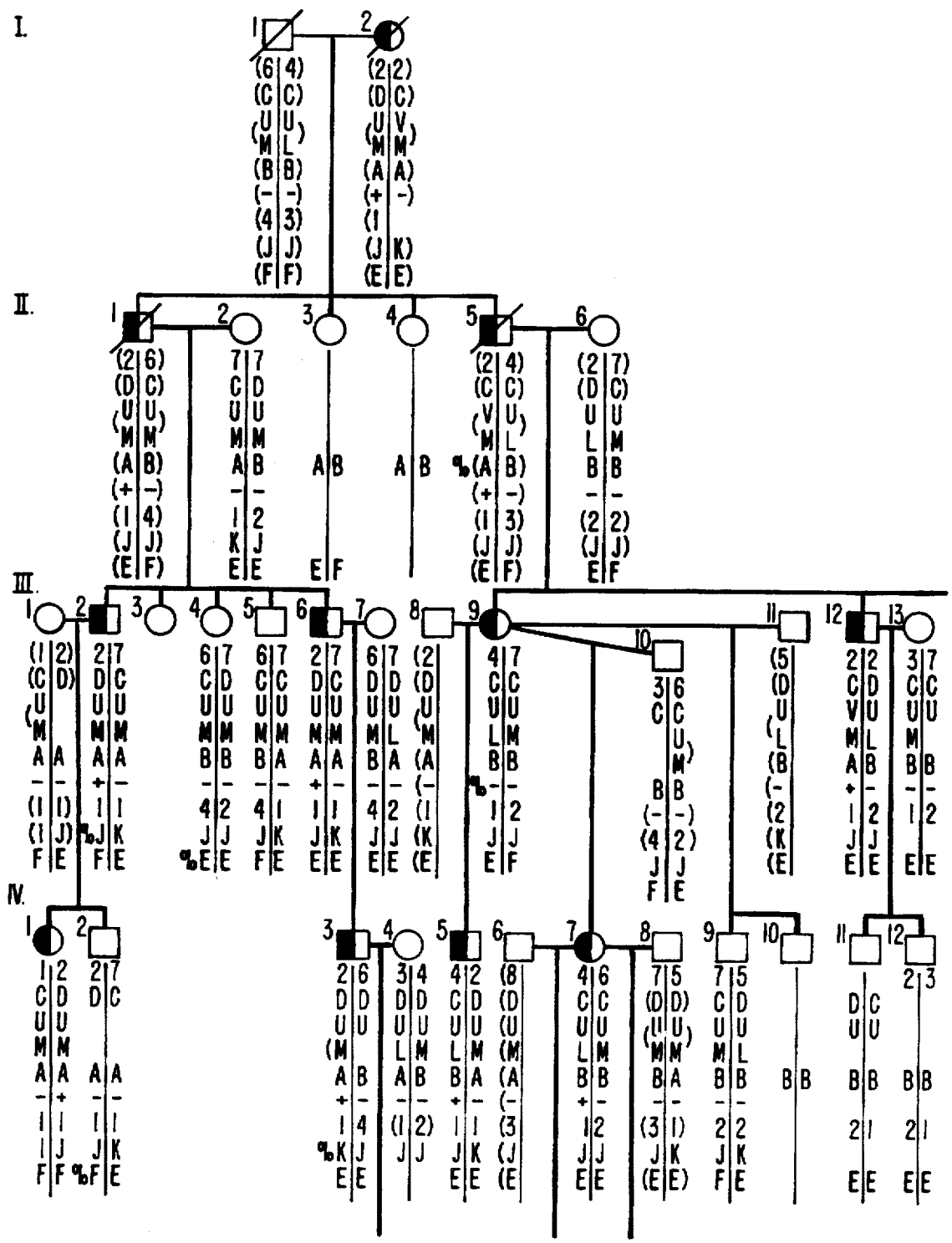
FIG. 2 illustrates the largest CMT1B pedigree.
Figure 2B:
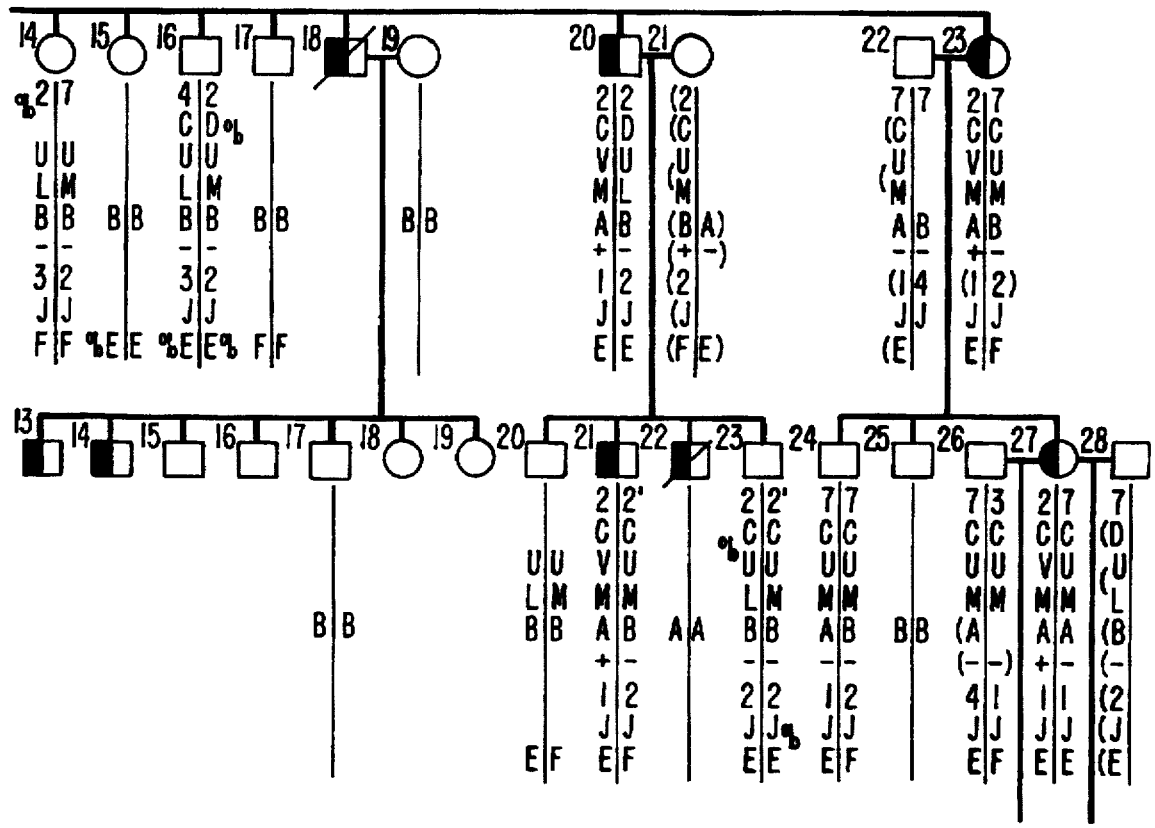
Figure 2C:
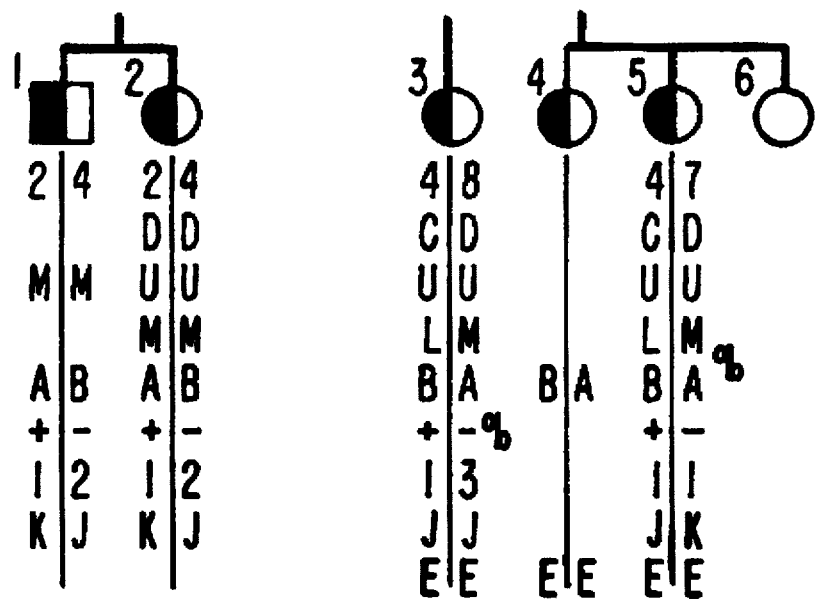
Figure 2:
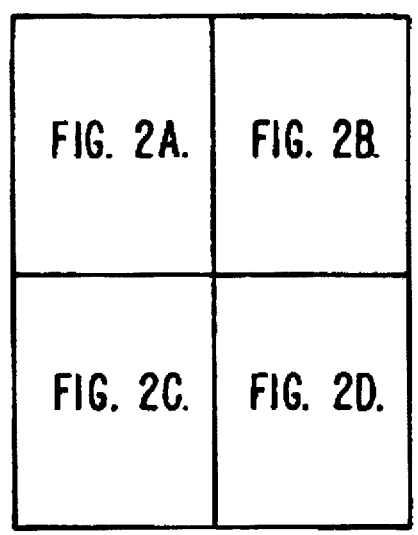
Figure 2D:
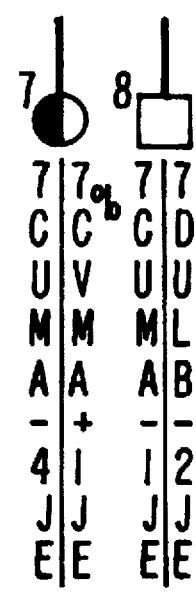

A P0 polymorphism was exhibited by affected individuals in the largest known pedigree (Pedigree 1). See FIG. 1. An A→G point mutation at nucleotide 115 in P0 exon 3 is carried by the abnormal CMT1B chromosome in Pedigree 1. The A→G transition identified in P0 at base pair 115 of exon 3 converts a TTCAAA P0 gene sequence to a palindromic BstBI restriction site TTCGAA. Thus, the normal amplified 163 base pair amplified sequence does not cut (−), but the mutated sequence can be digested to 115 and 48 base pair BstBI restriction fragments (+) in CMT1B Pedigree 1 patients. The 48 basepair fragment is too light to be scored. In Pedigree 1, amplifed segments from 17 of 17 CMT1B patients included the BstB1 site (FIG. 2), while all other subjects did not display this RFLP including 12 normal members of the same pedigree, 7 unrelated CMT1A patients with a chromosome 17 duplication, 31 unrelated CMT patients without the CMT1A duplication, and 18 randomly selected unrelated normal individuals. In FIG. 2, CMT patients are indicated by half-filled symbols for the autosomal dominant genetic disease. Inferred genotypes are indicated by parentheses.

Amplified nucleic acid segments were sequenced according to the method of Sanger. The only mutation identified in pedigree 1 was found in exon 3. Altogether, 282 unrelated chromosomes did not carry as A→G P0 mutation generating a BstB1 site in exon 3 of the gene.

This major mutation occurs in codon 96 of the P0 protein in a region of P0 with 36 identical amino acid sequences in 3 mammalian orders; human (primate), rat (rodent) and cow (artiodactyl) that diverged about one hundred million years ago (FIG. 4; Sakamoto et al., J. Biol. chem., 262:4208–4214 (1985); Lemke et al., *Cell*, 501–508 (1985)). The missense mutation (K96E) substitutes a negatively charged glutamic acid (E) for a positively charged lysine (K) in this conserved extracellular protein region (FIG. 4). Substitution of a negatively charged amino acid for a positive one in region of P0 protein required for adhesive binding to another P0 protein represents a major change most likely to disrupt P0 extracellular domain attachment. That this mutation occurred in a protein region conserved identically in three unrelated mammals emphasizes the importance of maintaining this protein structure without change.

Example 2

This example demonstrates significant linkage of the BstBI polymorphic site in the amplified segments with informative flanking markers. LOD scores exceeded 9 for some markers.

Linkage data were handled by the data management program LIPIN (Trofatter et al., *Am. J. Hum. Genet.*, 39:147–148 (1986)). Computer analysis of the segregation of the BstB1 PO polymorphic site and the five most informative flanking markers raised the multipoint LOD score to 7.9→9.2 at θ=0.00 (Table 1). This result confirmed the suggested CMT1B gene location in the 3 Mb chromosome region between the flanking loci ATP1A2 and 1054 loci. Because both flanking loci and the FcγRII locus co-segregated with the CMT1B phenotype in a second CMT1B pedigree without an A→G PO mutation (LOD=2.1; Lebo et al., *Human Genet.*, 88:1–12 (1991)), the PO locus adjacent to the FcγTRII locus must also co-segregate with the CMT1B phenotype (LOD=2.1; total multipoint LOD= 9.0→11.3; θ=0.00). Thus, the PO locus co-segregates with the CMT1B phenotype in each informative meiosis.

A298C11; CEPH: 12736=194H7 and 12738=248H4. Restriction analysis of human and yeast DNAs were carried out as previously described (Qiu et al., supra). The PO gene was cloned as follows: YAC 12736 was isolated in low melt agarose and restricted with BamHI. A library of these fragments was made in pBluescript according the the manufacturer's directions. The library was screened with a cloned human PO exon 6 probe made by PCR of total human DNA using mouse primers. A 10.2 kb clone was characterized that contained the cell PO coding region. In situ hybridization and pulsed field gel electrophoresis were performed as described in Lebo et al., *Human Genet.*, 88:13–20 (1991), previously incorporated herein by reference.

Example 4

This example demostrates the identification of multiple polymorphisms and mutations in CMT1B patients using the methods of the invention.

TABLE 1

| Conditioner Most-> Least likely | Recombination fractions between adjacent loci 0–0.5 | | | | | −2lnLocation loci | |
|---|---|---|---|---|---|---|---|
| FY-ATP1A2-PCGR2-PO-CMT1B-1054 | 0.05 | 0.04 | 0.00 | 0.00 | 0.15 | 304.698 | 9.19 |
| FY-ATP1A2-PCGR2-PO-CMT1B-1054 | 0.05 | 0.04 | 0.00 | 0.075 | 0.085 | 310.204 | 7.99 |
| FY-ATP1A2-CMT1B-PO-FCGR2-1054 | 0.05 | 0.01 | 0.03 | 0.00 | 0.15 | 310.592 | 7.91 |
| CMT1B-FY-ATP1A2-PO-PCGR2-1054 | 0.05 | 0.05 | 0.04 | 0.00 | 0.15 | 318.414 | 6.21 |
| FY-ATP1A2-PO-PCGR2-1054-CMT1B | 0.05 | 0.04 | 0.00 | 0.15 | 0.05 | 322.144 | 5.40 |
| FY-CMT1B-ATP1A2-PO-PCGR2-1054 | 0.02 | 0.03 | 0.04 | 0.00 | 0.15 | 325.806 | 4.60 |

Relative order ratios $10^{(x−y)}$ where x = more likely location score and y = least likely location score

| Order vs. 6 | | Order vs. 5 | | | Order vs. 4 | Order vs. 3 | Order vs. 2 |
|---|---|---|---|---|---|---|---|
| 1. 38,904.1 | | 1. 6165.9 | 1. 961.8 | | 1. 19.1 | 1. 15.9 | |
| 2. 2,454.7 | 2. 389.0 | 2. 60.7 | 2. 1.2 | | | | |
| 3. 2,041.7 | 3. 323.6 | 3. 50.4 | | | | | |
| 4. 40.4 | 4. 6.4 | | | | | | |
| 5. 6.3 | | | | | | | |

Example 3

Figure 3:
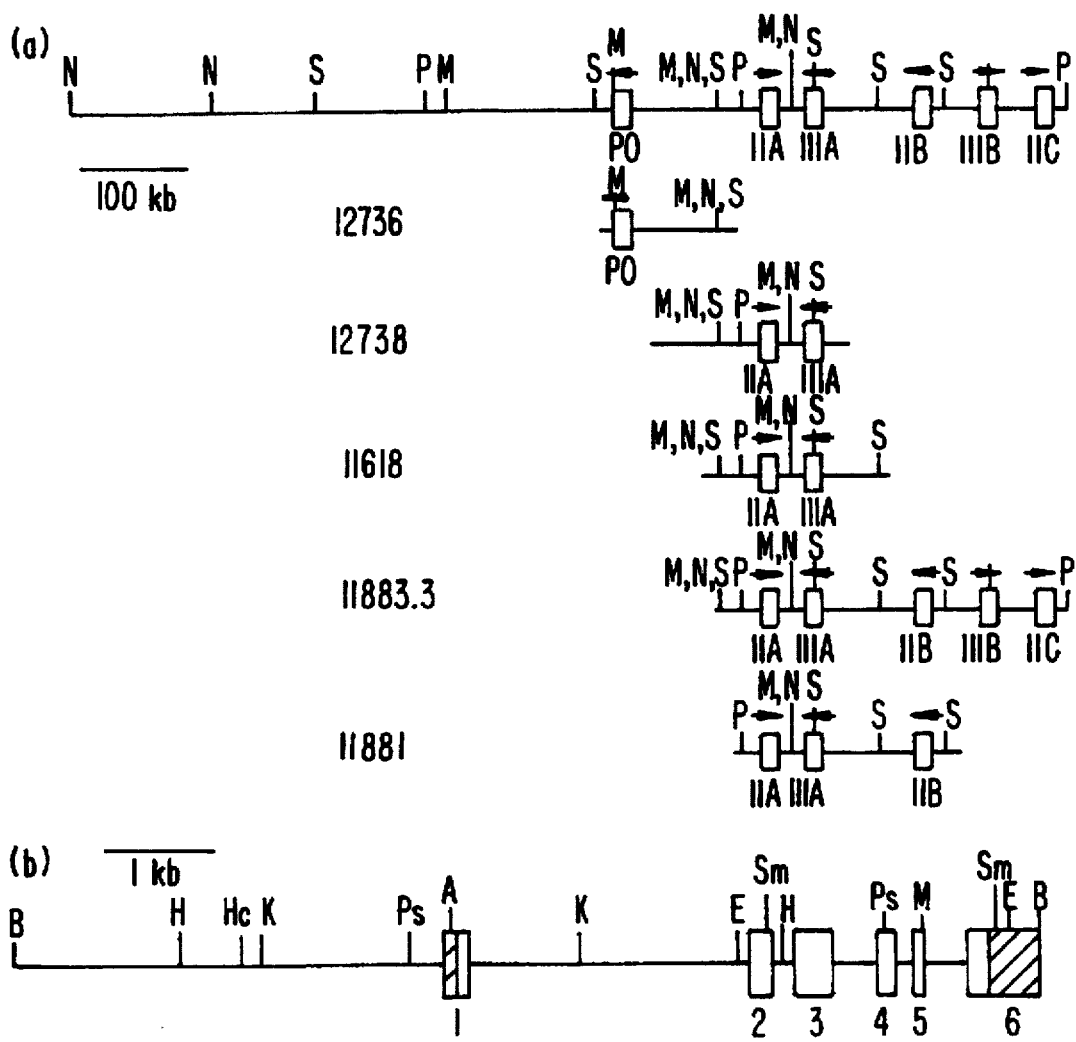
FIG. 3 illustrates the physical map of the human chromosome 1q22 protein P0 gene region.

This example demonstrates localization of the PO gene on 1q22. To localize this gene on 1q22, YAC clones were isolated to this region of the chromosome. A 900 kb YAC contig spanning the Fcγ receptor gene complex was used to sublocalize the PO gene 150 kb centromeric to the Fcγ RIIA locus (FIG. 3A). Restriction sites common to human genomic DNA (top line) and YACs (bottom) are indicated. M:MluI; P:PmeI; N:NruI; S:SfiI. Boxes indicate positions of known genes and arrowheads denote their transcriptional orientation. This location is consistent with the homologous mouse linkage map (Oakey et al., *Human Molec. Genet.*, 1:613–620 (1992)). Fluorescence in situ hybridization with a 10kb PO gene subclone from YAC 12736 (FIG. 3A) confirmed the PO assignment uniquely to band 1q22 in close proximity to the Fcγ receptor complex. The human PO gene intron-exon structure was determined from the YAC subclone (FIG. 3B) and used to determine sequence relationship between normal and CMT1B individuals. In FIG. 3B, boxes indicate exons and cross hatching denotes untranslated regions. A:ApaI, B:BamHI; E:EcoRI; H:HindIII; Hc:HincII; K:KpaI; M:MluI; Ps:PatI; Sm:SmaI.

YACs containing IgG Fc receptor II and III genes were isolated from the St. Louis YAC library as previously reported Qiu et al., *Science*, 248:732–735 (1990), incorporated herein by reference. Additional YACs were derived from a CEPH library by walking with a probe from the centromeric end of YAC 11618. The YACs included in this report are identified in their respective libraries as follows. St. Louis 11618=A104C1; 11881=A298B5 and 11883.3=

Using the approach set forth above, a total of 19 primers (Table 2) that can be used as 16 primer pairs (Table 3) to amplify and sequence each of the 6 human PO gene exons.

Figure 5:
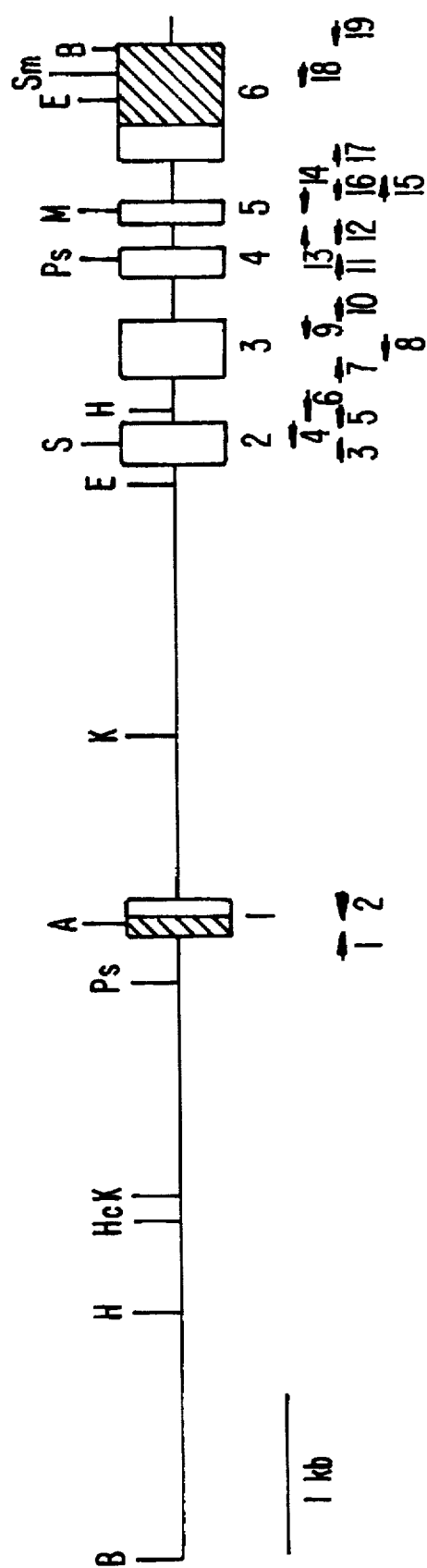
FIG. 5 is a restriction map of the P0 gene.

FIG. 5 is a schematic diagram of the 6 PO gene exons along with a restriction map of the gene. The locations of the primers listed in Table 2 are shown there, as well. Using these primer pairs, each of the gene's six exons were amplified in CMT patients without the most common form of CMT, the CMT1A duplication, as determined by another diagnostic test. These results found 11 polymorphic sites spread throughout the coding sequence with at least one polymorphic site in each of the six exons (Table 4). We also found 4 unique mutation sites in 3 CMT1B patients (Table 5). These data demonstrate that this is the most appropriate means to identify CMT1B mutations among patients without CMT1A duplications.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail byway of illustration and example for purposes of clarity of understanding, it will be obvious that certain changes and modifications may be practiced within the scope of the appended claims.

TABLE 2

MPZ Primer Pair Sequences.

| Primer/Direction | Lab # | Exon# | Description | Sequence |
|---|---|---|---|---|
| 1 /F | 2638 | 1 | 5' untranslated region | CTC AAC CCC ACA GAT GCT C |
| 2 /R | 2639 | 1 | 3'end of exon 1 | CCA AAG AAG AGA AGA GCA GC |
| 3 /F | 2652 | 2 | 5' exon + splice site | AGT GCT GTC CCC GGC CC |
| 4 /R | 2655 | 2 | 3' exon + splice site | CCG AAA TGG CAT CTC TGC C |
| 5 /R | 74 | 2 | within intron 2 | GAA GCA CTT TCT GTT ATC C |
| 6 /R | 73 | 2 | within intron 2 | CCC TCC TTA GCC CAA GTT ATC T |
| 7 /F | 42 | 3 | in exon 3; 3 bp from 5' end | ATC TTC CAC TAT GCC AAG GGA C |
| 9 /R | 2650 | 3 | 3' exon 3 + splice site | ACC TTT TTC AAA GAC ATA CAG C |
| 10 /R | 2662 | 3 | within intron 3 | AGA TCT TCC ACT ATG CCA AGG G |
| 11 /F | 2640 | 4 | 5' exon 4 + splice site | AGT GCC AAC TAG GTA CGG G |
| 12 /R | 72 | 4 | within intron 4 | TGG AGT AGT CTC CGC CCA GAT |
| 13 /F | 75 | 5 | within intron 4 | ATC TGG GCG GAG ACT ACT CCA |
| 14 /R | 2644 | 5 | 3' exon 5 + splice site | ACC TGC CGC CCG CGC TT |
| 16 /R | 2665 | 5 | intron 5 region | CCA TCC CAC CCC TCA CTG CTG CCC GG |
| 17 /F | 71 | 6 | intron 5 | TCG GTG ACT GAT GTG TGC GC |
| 18 /R | 41 | 6 | within exon 6; 5 bp to stop codon | TAT CCT TGC GAG ACT CCC CC |
| 19 /R | 2641 | 6 | 3' untranslated region | GCC TTT GGC GGA CTC CAC |

Determines entire 747 amino acid gene sequence with ABI automated sequencer.
Determines 97% of sequencing with standard gel electrophoresis and autoradiography.

TABLE 3

MPZ Primer Sequencing Strategy.[a]

| Exon Amplified | PCR Primer Pair | Optimal Sequencing Primer(s)[b] |
|---|---|---|
| 1 | 1 + 2 | 1 |
| 2 | 3 + 6 | 6 |
| 2 | 3 + 6 | 5 |
| 2 | 3 + 4 |   |
| 3 | 7 + 10 | 10 |
| 3 | 7 + 9 |   |
| 4 | 11 + 12 | 12 |
| 5 | 13 + 16 | 16 |
| 5 | 13 + 14 | 13 |
| 6 | 17 + 19 | 19 |
| 6 | 17 + 19 | 17 |

| Intron Amplified | PCR Primer Pair | Optimal Sequencing Primer(s)* |
|---|---|---|
| 2 | 3 + 9 |   |
| 3 + 4 | 7 + 14 |   |
| 3 + 4 | 7 + 16 |   |
| 4 + 5 | 11 + 19 |   |
| 1 | 1 + 4[c] |   |

[a] Optimal sequencing primers are listed in the preferred order for each exon tested.
[b] Amplifications from total genomic DNA.
[c] Amplifies only cloned DNA uniquely

TABLE 4

MPZ POLYMORPHISM SUMMARY**

| EXON | RESTRICTION SITE | NUCLEOTIDE CHANGE (Position) | AMINO ACID CHANGE | Minor Allele Frequency |
|---|---|---|---|---|
| 1 | ScrFI | C->A(83) | Leu->Met | .40/.60 |
| 2 | no site | G->A(269) | Ala->Thr Ala->Ser | .14/.33/.52 |
| 3 | HhaI | G->A(334) | Glu->Glu | .11/.89 |
| 3 | no site | A->C(431) | Lys->Gln | .28/.72 |
| 4 | AluI | G->A(521) | Ala->Thr | .39/.61 |
| 4 | no site* | G->C(562) | Leu->Leu | .15/.85 |
| 4 | no site | T->C(572) | His->Tyr | .44/.66 |
| 4 | EcoRII | G->C(588) | Cys->Ser | .15/.85 |
| 5 | no site | G->T(649) | Leu->Phe | .47/.53 |
| 5 | no site | G->A(655) | Lys->Lys | .47/.53 |
| 6 | no site | G->T(760) | Gly->Gly | .22/.78 |

*Fnu4HI no good; flanked by identical sites
**Based upon single direction sequencing

TABLE 5

MPZ MUTATION SUMMARY

| PATIENT I.D. | EXON | RESTRICTION SITE | NUCLEOTIDE CHANGE (Position)[+] | AMINO ACID CHANGE |
|---|---|---|---|---|
| 3551 | 6 | no site | G->T(741) | Ser->Ile* S233I |
| 3641 | 6 | no site | A->T(732) | Lys->Ile*[1] K230I |
| 3645 | 6 | AluI | G->C(734) | Ala->Pro* A231P |
|   | 3 | ScrFI | G->C(360)[1] | Arg->Pro R106P |

*Major mutation based upon bidirectional sequencing and amino acid characteristics and comparison of human, rat, and cow protein sequences.
[1] Based upon clear unidirectional sequencing results.
[+] Corresponds to database humspm sequence.

What is claimed is:

1. A composition for detection of a gene associated with Charcot-Marie-Tooth Disease Type 1B comprised of two amplification primers, wherein the first amplification primer is to

TTC CAC TAT GCC AAG GGA CAA C; (SEQ ID NO:1).

and the second amplification primer is to

CTG GTG GGT TTT TGA CAT CAC AT (SEQ ID NO:2).

2. A kit for the detection of genetic polymorphisms associated with Charcot-Marie-Tooth Disease Type 1B, comprising a vial containing SEQ ID NO:1 and SEQ ID NO:2.

3. A kit as in claim 2, further comprising a vial containing a thermostable polymerase.

4. A composition for the detection of a gene associated with Charcot-Marie-Tooth Disease Type B, comprising a first oligonucleotide which binds substantially to the first intron located upstream of human myelin protein zero (P0) gene exon 2, and a second oligonucleotide which binds substantially to the second intron located downstream of human protein zero (P0) gene exon 2.

5. A composition for the detection of a gene associated with Charcot-Marie-Tooth Disease Type B, comprising a first oligonucleotide which binds substantially to the intron located upstream of human myelin protein zero (P0) gene exon 3, and a second oligonucleotide which binds substantially to the intron located downstream of human protein zero (P0) gene exon 3.

6. A composition for the detection of a gene associated with Charcot-Marie-Tooth Disease Type B, comprising a first oligonucleotide which binds substantially to the intron located upstream of human myelin protein zero (P0) gene exon 4, and a second oligonucleotide which binds substantially to the intron located downstream of human protein zero (P0) gene exon 4.

7. A composition for the detection of a gene associated with Charcot-Marie-Tooth Disease Type B, comprising a first oligonucleotide which binds substantially to the intron located upstream of human myelin protein zero (P0) gene exon 5, and a second oligonucleotide which binds substantially to the intron located downstream of human protein zero (P0) gene exon 5.

8. A composition for the detection of a gene associated with Charcot-Marie-Tooth Disease Type B, comprising a first oligonucleotide which binds substantially to the intron located upstream of human myelin protein zero (P0) gene exon 6, and a second oligonucleotide which binds substantially to the intron located downstream of human protein zero (P0) gene exon 6.

9. A method for detecting the presence of a genetic polymorphism associated with Charcot-Marie-Tooth Disease Type 1B in a sample of patient nucleic acid, comprising:

contacting the sample with an oligonucleotide which binds specifically to a nucleic acid subsequence of a human myelin protein zero (P0) gene, and detecting hybridization of the oligonucleotide to the human myelin protein zero (P0) gene subsequence;

whereby detecting hybridization of the oligonucleotide provides a determination that the sample contains a genetic polymorphism associated with Charcot-Marie-Tooth Disease Type 1B.

10. A method as in claim 9, wherein the sample of patient nucleic acid comprises chromosomal DNA.

11. A method as in claim 10, wherein the chromosomal DNA is chromosome 1.

12. A method as in claim 9, wherein the subsequence is in an exon.

13. A method as in claim 12, wherein the exon is selected from the group consisting of human myelin protein zero (P0) gene exon 1, exon 2, exon 3, exon 4, exon 5, and exon 6.

14. A method as in claim 9, further comprising digesting the nucleic acid with a restriction enzyme to produce restriction fragments.

15. A method as in claim 14, wherein the restriction enzyme is selected from the group consisting of BstBI, ScrFI, HhaI, AluI, and EcoRII.

16. A method as in claim 14, further comprising separating the restriction fragments by gel electrophoresis.

17. A method as in claim 16, wherein the Charcot-Marie-Tooth Disease Type 1B polymorphism is identified by the migration pattern of the restriction fragments on the gel.

18. A method as in claim 16, wherein the gel electrophoresis is polyacrylamide gel electrophoresis.

19. A method as in claim 9, wherein the step of detecting hybridization of the oligonucleotide comprises amplifying the human myelin protein zero (P0) gene subsequence.

20. A method as in claim 9, wherein the subsequence is in a human myelin protein (P0) gene intron.

21. A method for detecting the presence of a genetic polymorphism associated with Charcot-Marie-Tooth Disease Type 1B in a sample of patient nucleic acid, comprising:

digesting the sample with a restriction enzyme to produce restriction fragments, separating the restriction fragments, contacting the fragments with an oligonucleotide that hybridizes to a nucleic acid subsequence of a human myelin protein zero (P0) gene, and detecting hybridization of the oligonucleotide to the human myelin protein zero (P0) gene subsequence;

whereby detecting hybridization of the oligonucleotide provides a determination that the sample contains a genetic polymorphism associated with Charcot-Marie-Tooth Disease Type 1B.

22. A method as in claim 21, wherein the restriction enzyme is selected from the group consisting of BstBI, ScrFI, HhaI, AluI, and EcoRII.

23. A method as in claim 21, wherein the subsequence is in an exon.

24. A method as in claim 23, wherein the exon is selected from the group consisting of human myelin protein zero (P0) gene exon 1, exon 2, exon 3, exon 4, exon 5, and exon 6.

* * * * *

UNITED STATES PATENT AND TRADEMARK OFFICE
CERTIFICATE OF CORRECTION

PATENT NO. : 5,723,593
DATED : March 3, 1998
INVENTOR(S) : Roger V. Lebo and Jeffrey Ravetch It is certified that error appears in the above-identified patent and that said Letters Patent is hereby corrected as shown below:

In the Claims

Claim 1, column 22, line 62, after "wherein", delete "the" and insert --a--, after "first", delete "amplification primer" and insert --oligonucleotide--, after "is", delete "to".

Claim 1, column 22, line 67, after "and", delete "the" and insert --a--, after "second", delete "amplification primer" and insert --oligonucleotide--, and after "is", delete "to".

Claim 1 with these corrections therefore reads:

1. A composition for detection of a gene associated with Charcot-Marie-Tooth Disease Type 1B comprised of two amplification primers, wherein a first oligonucleotide is

TTC CAC TAT GCC AAG GGA CAA C; (SEQ ID NO:1).

and a second oligonucleotide is

CTG GTG GGT TTT TGA CAT CAC AT (SEQ ID NO:2).

Claims 4-8, delete "Type B" and insert --Type 1B--

Signed and Sealed this

Twenty-third Day of June, 1998

Attest:

BRUCE LEHMAN

*Attesting Officer*                 *Commissioner of Patents and Trademarks*